United States Patent
Ruaan et al.

(10) Patent No.: US 10,322,188 B2
(45) Date of Patent: Jun. 18, 2019

(54) CELL-PENETRATING DRUG CARRIER AND THE APPLICATION THEREOF

(71) Applicant: National Central University, Taoyuan (TW)

(72) Inventors: Ruoh-Chyu Ruaan, Taipei (TW); Ching-Wei Tsai, Taoyuan (TW); Chuan-Hui Lu, Pingtung County (TW); Yung Chang, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 467 days.

(21) Appl. No.: 14/799,747

(22) Filed: Jul. 15, 2015

(65) Prior Publication Data
US 2016/0120998 A1    May 5, 2016

(30) Foreign Application Priority Data
Jul. 18, 2014   (TW) .............................. 103124817 A

(51) Int. Cl.
| | |
|---|---|
| *C07K 7/06* | (2006.01) |
| *A61K 47/48* | (2006.01) |
| *A61K 31/704* | (2006.01) |
| *A61K 47/60* | (2017.01) |
| *A61K 47/64* | (2017.01) |

(52) U.S. Cl.
CPC ...... *A61K 47/48246* (2013.01); *A61K 31/704* (2013.01); *A61K 47/60* (2017.08); *A61K 47/64* (2017.08); *C07K 7/06* (2013.01); *C07K 2319/10* (2013.01); *C07K 2319/70* (2013.01)

(58) Field of Classification Search
None
See application file for complete search history.

(56) References Cited

U.S. PATENT DOCUMENTS

2010/0111866 A1* 5/2010 Kratz ............... A61K 47/48238
424/9.1

OTHER PUBLICATIONS

Harris et al. (Small. Sep. 2008; 4(9): 1307-1312) (Year: 2008).*
Santa Cruz (downloaded online from URL:<http://datasheets.scbt.com/sc-206015.pdf>) (Year: 2009).*
Shi et al. (International Journal of Nanomedicine 2012:7 1613-1621) (Year: 2012).*

\* cited by examiner

*Primary Examiner* — Sergio Coffa
(74) *Attorney, Agent, or Firm* — WPAT, PC

(57) ABSTRACT

This invention is about a cell-penetrating drug carrier and the application thereof. The mentioned cell-penetrating drug carrier can approach the target cell through using a proper recognizable sequence, so that the cell-penetrating drug carrier can be used to specifically delivery wanted drug to target cell. Through carrying wanted drug into the cytoplasm of the target cell by cell-penetrating peptide, the drug accumulation volume in the target cell can be efficiently increased. Preferably, through using proper bioinert polymer, the cell-penetrating peptide and the recognizable sequence can be kept from been digested before approaching the target cell.

15 Claims, 11 Drawing Sheets

Specification includes a Sequence Listing.

CELL-PENETRATING DRUG CARRIER AND THE APPLICATION THEREOF

BACKGROUND OF THE INVENTION

1. Field of the Invention

The present invention is generally related to a drug carrier, and more particularly to a cell-penetrating drug carrier and the application thereof.

2. Description of the Prior Art

It is very general for people using medicine to cure diseases. "Applying medicine according to indications" means using corresponding medicine to the target disease. The medicine can be applied as oral medication, intravenous injection, or external application. In the recently years, people have more idea about therapy. For example, on curing tumor cells, if the drug can be safely and precisely carried to target region by proper carrier, the dose and side-reaction of the drug can be reduced. Therefore, how to develop proper drug carrier becomes a hot issue.

For small molecule drugs, the recently drug carrier types are nanoparticles, hydrogel, liposome, micelle, and cell-penetrating peptide (CPP). While employing the first four types of carriers, the medicinal property of the wanted drug must be considered. Those four types of carriers can transport the wanted drug by covering, physical absorption, or chemical grafting. For instance, liposome employs at least two phospholipid layers to cover the wanted drug for transportation, and the lifetime in vivo circulation of the wanted drug can be extended. As known by one skilled in the art, the first four carrier types need expensive carrier design, and those four carrier types cannot provide good specifically delivery for wanted drug.

CPP is a novel drug carrier technology. CPP can precisely carry wanted drug to target position, and keep the wanted drug from decomposition before achieving the target position. Moreover, cell-penetrating peptide can carry the wanted drug into the cytoplasm of the target cell, and the drug accumulation volume in the target cell can be efficiently increased. So that the dose of the wanted drug can be reduced, and the side-reaction of the wanted drug can be decreased.

In view of the above matter, developing a novel cell-penetrating drug carrier and the application thereof having specifically delivery of wanted drug, and being able to increase drug accumulation volume in the target cell and decrease the dose and side-reaction of the wanted drug is still an important task for the industry.

SUMMARY OF THE INVENTION

In light of the above background, in order to fulfill the requirements of the industry, the present invention provides a novel cell-penetrating drug carrier and the application thereof. The mentioned cell-penetrating drug carrier and the application thereof can be produced by simple manufacture and does not cost expensively. Preferably, the cell-penetrating drug carrier and the application thereof can efficiently decrease the dose of the wanted drug and the side-reaction of the wanted drug. More preferably, the mentioned cell-penetrating drug carrier and the application thereof can modify the dug carrier structure with the target cell and the wanted drug, so that the drug safety and the industrial competitive can be efficiently advanced.

One object of the present invention is to provide a cell-penetrating drug carrier and the application thereof, through connecting a cell-penetrating peptide with a wanted drug, the wanted drug can be carried into the cytoplasm of the target cell by the cell-penetrating peptide, and the drug accumulation volume in the target cell can be efficiently increased.

Another object of the present invention is to provide cell-penetrating drug carrier and the application thereof, through connected a recognizable sequence with a cell-penetrating peptide, when the cell-penetrating drug carrier transported to the target cell, the recognizable sequence will be recognized and cut by the enzyme at the neighborhood of the target cell, and the wanted drug will be released, so that the cell-penetrating drug carrier of this application can provide specifically delivery of wanted drug to target cell.

Still another object of the present invention is to provide cell-penetrating drug carrier and the application thereof, through employing a bioinert polymer to protect the cell-penetrating peptide and the recognizable sequence of the cell-penetrating drug carrier, the decomposition of the wanted drug during circulation can be decreased, so that the lifetime of the wanted drug in circulation can be extended, and the opportunity for the cell-penetrating drug carrier carrying the wanted drug to the target cell can be optimized.

Accordingly, the present invention discloses a cell-penetrating drug carrier and the application thereof. The cell-penetrating drug carrier comprises cell-penetrating peptide, recognizable sequence, and bioinert polymer. There are two ends of the mentioned cell-penetrating peptide connected with a wanted drug and the recognizable sequence individually. In one preferred example of this specification, the C-terminus of the cell-penetrating peptide is connected with the wanted drug, and the N-terminus of the cell-penetrating peptide is connected with the recognizable sequence. The mentioned wanted drug can be small molecule drug.

In one preferred example of this specification, the mentioned cell-penetrating peptide can be Indolicidin (IL; ILPWKWPWWPWRR; SEQ ID NO: 1) analogue. The mentioned cell-penetrating peptide can be selected from one of the group consisting of the following: Indolicidin (IL; ILPWKWPWWPWRR; SEQ ID NO: 1), ILR57F89 (ILPWRWRFFPWRR; SEQ ID NO: 2).

In one preferred example of this specification, the mentioned recognizable sequence can be a peptide recognized by matrix metalloproteinase (MMP). The matrix metalloproteinase can be selected from matrix metalloproteinase-2 (MMP-2), matrix metalloproteinase-9 (MMP-9). In one preferred example, the mentioned recognizable sequence can be selected from one of the group consisting of the following: Gly-Pro-Leu-Ser-Ile (SEQ ID NO: 3), Gly-Pro-Leu-Gly-Ile (SEQ ID NO: 4), wherein the "Ile" can be from the mentioned cell-penetrating peptide or other peptide.

In one preferred example of this specification, the mentioned bioinert polymer is a polymer with biocompatibility. The mentioned bioinert polymer can form a protecting layer surrounding the cell-penetrating peptide and the recognizable sequence. The bioinert polymer can keep the cell-penetrating drug carrier from cutting by enzyme before achieving the target cell, so that the lifetime of the cell-penetrating drug carrier in vivo circulation can be extended. In one preferred example, the mentioned bioinert polymer can be polyethylene glycol (PEG), and the average molecular weight of the bioinert polymer is about 1000-25000. In one preferred example of this specification, when the C-terminus of the cell-penetrating peptide connected with the wanted drug, the bioinert polymer can be connected with the N-terminus of the recognizable sequence. In another preferred example of this specification, when the N-terminus of the cell-penetrating peptide connected with the wanted drug, the bioinert polymer can be connected with the C-terminus of the recognizable sequence.

In one preferred example of this specification, the cell-penetrating drug carrier can further comprise a first cross-linker. The first cross-linker is between the mentioned cell-penetrating peptide and the wanted drug, and the first cross-linker is used to connect the cell-penetrating peptide and the wanted drug. In one preferred example, the mentioned first cross-linker comprises a peptide consisted of 3-5 amino acids. In another preferred example, the first cross-linker can be selected from one of the group consisting of the following: APDP (N-[4-(p-Azido-salicylamido)butyl]-3'-(2'-pyridyldithio)), Sulfo-SAED [Sulfosuccinimidyl 2-(7-azido-4-methylcoumarin-3-acetamido)ethyl-1,3 dithiopropionatepropionamide], Sulfo-SAED [Sulfosuccinimidyl 2-(7-azido-4-methylcoumarin-3-acetamido)ethyl-1,3 dithiopropionate], EMCS [N-(ε-Maleimidocaproyloxy)succinimide ester], GMBS [N-(γ-Maleimidobutyryloxy)succinimide ester], SMCC [Succinimidyl 4-(N-maleimido-methyl)cyclohexane-1-carboxylate], SMPB [Succinimidyl 4-(p-maleimido-phenyl)butyrate].

In one preferred example of this specification, the cell-penetrating drug carrier can further comprise a second cross-linker. The second cross-linker is between the mentioned cell-penetrating peptide and the recognizable sequence, and the second cross-linker is used to connect the cell-penetrating peptide and the recognizable sequence. In one preferred example, the mentioned second cross-linker comprises peptide consisted of 3-5 amino acids. In another preferred example, the second cross-linker can be selected from one of the group consisting of the following: APDP (N-[4-(p-Azido-salicylamido)butyl]-3'-(2'-pyridyldithio)), Sulfo-SAED [Sulfosuccinimidyl 2-(7-azido-4-methylcoumarin-3-acetamido)ethyl-1,3 dithiopropionatepropionamide], Sulfo-SAED [Sulfosuccinimidyl 2-(7-azido-4-methylcoumarin-3-acetamido)ethyl-1,3 dithiopropionate], EMCS [N-(ε-Maleimidocaproyloxy)succinimide ester], GMBS [N-(γ-Maleimidobutyryloxy)succinimide ester], SMCC [Succinimidyl 4-(N-maleimido-methyl)cyclohexane-1-carboxylate], SMPB [Succinimidyl 4-(p-maleimido-phenyl)butyrate].

In one preferred example of this specification, the cell-penetrating drug carrier can further comprise a third cross-linker. The third cross-linker is between the mentioned recognizable sequence and the bioinert polymer, and the third cross-linker is used to connect the recognizable sequence and the bioinert polymer. In one preferred example, the mentioned third cross-linker comprises a peptide consisted of 3-5 amino acids. In another preferred example, the third cross-linker can be selected from one of the group consisting of the following: APDP (N-[4-(p-Azido-salicylamido)butyl]-3'-(2'-pyridyldithio)), Sulfo-SAED [Sulfosuccinimidyl 2-(7-azido-4-methylcoumarin-3-acetamido)ethyl-1,3 dithiopropionatepropionamide], Sulfo-SAED [Sulfosuccinimidyl 2-(7-azido-4-methylcoumarin-3-acetamido)ethyl-1,3 dithiopropionate], EMCS [N-(ε-Maleimidocaproyloxy)succinimide ester], GMBS [N-(γ-Maleimidobutyryloxy)succinimide ester], SMCC [Succinimidyl 4-(N-maleimido-methyl)cyclohexane-1-carboxylate], SMPB [Succinimidyl 4-(p-maleimido-phenyl)butyrate].

DESCRIPTION OF THE PREFERRED EMBODIMENTS

Figure 1A:
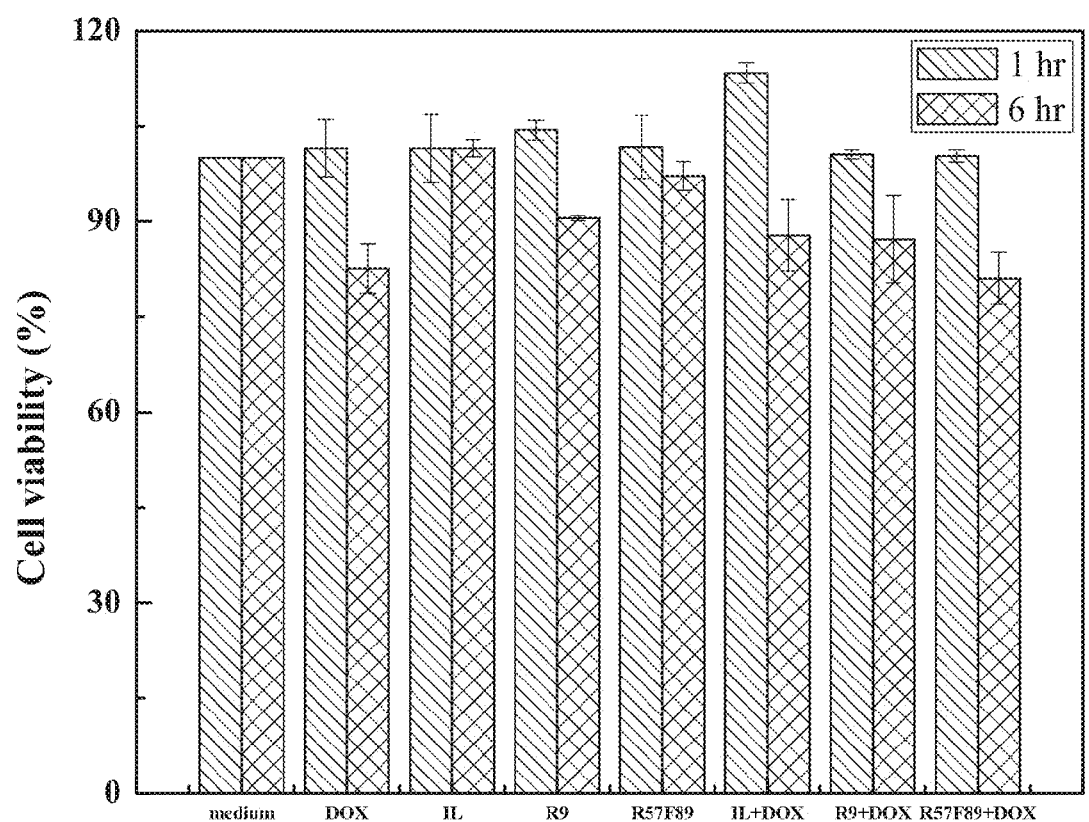
FIG. 1A shows the cell viability test results of HepG2 with DOX, IL, IL-R57F89, mixture of DOX and IL, and mixture of DOX and IL-R57F89 for 1 hour and for 6 hours.

What probed into the invention is cell-penetrating drug carrier and the application thereof. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One preferred embodiment according to this specification discloses a cell-penetrating drug carrier. The cell-penetrating drug carrier comprises cell-penetrating peptide (CPP), recognizable sequence, and bioinert polymer. There are two ends of the cell-penetrating peptide connected with a wanted drug and the mentioned recognizable sequence individually. According to this embodiment, the mentioned cell-penetrating peptide can be Indolicidin (IL; ILPWKWPWWPWRR) analogue. In one preferred example of this embodiment, the mentioned cell-penetrating peptide can be selected from one of the group consisting of the following: Indolicidin (IL; ILPWKWPWWPWRR; SEQ ID NO: 1), ILR57F89 (ILPWRWRFFPWRR; SEQ ID NO: 2). In one preferred example of this embodiment, the mentioned wanted drug can be small molecule drug. In one preferred example, the mentioned wanted drug can be doxorubicin (DOX).

According to this embodiment, the recognizable sequence can be peptide, wherein the peptide can be recognized by matrix metalloproteinase (MMP). The matrix metalloproteinase can be selected from matrix metalloproteinase-2 (MMP-2), matrix metalloproteinase-9 (MMP-9). In one preferred example of this embodiment, the mentioned recognizable sequence can be selected from one of the group consisting of the following: Gly-Pro-Leu-Ser-Ile (SEQ ID NO: 3), Gly-Pro-Leu-Gly-Ile (SEQ ID NO: 4), wherein the "Ile" can be from the mentioned cell-penetrating peptide or other peptide.

The mentioned bioinert polymer can be connected with the mentioned recognizable sequence. According to this embodiment, the mentioned bioinert polymer can be a polymer with biocompatibility. The mentioned bioinert polymer can form a protecting layer surrounding the cell-penetrating peptide and the recognizable sequence. The bioinert polymer can keep the cell-penetrating drug carrier from cutting by enzyme before achieving the target cell, so that the lifetime of the cell-penetrating drug carrier in vivo circulation can be extended. In one preferred example of this embodiment, the mentioned bioinert polymer can be polyethylene glycol (PEG), and the average molecular weight of the bioinert polymer is about 1000-25000.

In one preferred example of this embodiment, the cell-penetrating drug carrier can further comprise a first cross-linker. The first cross-linker is between the mentioned cell-penetrating peptide and the wanted drug. The first cross-linker is used to connect the cell-penetrating peptide and the wanted drug. In one preferred example, the first cross-linker comprises peptide consisted of 3-5 amino acids. In another preferred example, the first cross-linker can be selected from one of the group consisting of the following: APDP (N-[4-(p-Azido-salicylamido)butyl]-3'-(2'-pyridyldithio)), Sulfo-SAED [Sulfosuccinimidyl 2-(7-azido-4-methylcoumarin-3-acetamido)ethyl-1,3 dithiopropionatepropionamide], Sulfo-SAED [Sulfosuccinimidyl 2-(7-azido-4-methylcoumarin-3-acetamido)ethyl-1,3 dithiopropionate], EMCS [N-(ε-Maleimidocaproyloxy)succinimide ester], GMBS [N-(γ-Maleimidobutyryloxy)succinimide ester], SMCC [Succinimidyl 4-(N-maleimido-methyl)cyclohexane-1-carboxylate], SMPB [Succinimidyl 4-(p-maleimido-phenyl)butyrate].

In one preferred example of this embodiment, the cell-penetrating drug carrier can further comprise a second cross-linker. The second cross-linker is between the mentioned cell-penetrating peptide and the mentioned recognizable sequence. The second cross-linker is used to connect the cell-penetrating peptide and the recognizable sequence. In one preferred example, the mentioned second cross-linker comprises peptide consisted of 3-5 amino acids. In another preferred example, the second cross-linker can be selected from one of the group consisting of the following: APDP (N-[4-(p-Azido-salicylamido)butyl]-3'-(2'-pyridyldithio)), Sulfo-SAED [Sulfosuccinimidyl 2-(7-azido-4-methylcoumarin-3-acetamido)ethyl-1,3 dithiopropionatepropionamide], Sulfo-SAED [Sulfosuccinimidyl 2-(7-azido-4-methylcoumarin-3-acetamido)ethyl-1,3 dithiopropionate], EMCS [N-(ε-Maleimidocaproyloxy)succinimide ester], GMBS [N-(γ-Maleimidobutyryloxy)succinimide ester], SMCC [Succinimidyl 4-(N-maleimido-methyl)cyclohexane-1-carboxylate], SMPB [Succinimidyl 4-(p-maleimido-phenyl)butyrate].

In one preferred example of this embodiment, the cell-penetrating drug carrier can further comprise a third cross-linker. The third cross-linker is between the recognizable sequence and the bioinert polymer. The third cross-linker is used to connect the recognizable sequence and the bioinert polymer. In one preferred example, the mentioned third cross-linker comprises peptide consisted of 3-5 amino acids. In another preferred example, the third cross-linker can be selected from one of the group consisting of the following: APDP (N-[4-(p-Azido-salicylamido)butyl]-3'-(2'-pyridyldithio)), Sulfo-SAED [Sulfosuccinimidyl 2-(7-azido-4-methylcoumarin-3-acetamido)ethyl-1,3 dithiopropionatepropionamide], Sulfo-SAED [Sulfosuccinimidyl 2-(7-azido-4-methylcoumarin-3-acetamido)ethyl-1,3 dithiopropionate], EMCS [N-(ε-Maleimidocaproyloxy)succinimide ester], GMBS [N-(γ-Maleimidobutyryloxy)succinimide ester], SMCC [Succinimidyl 4-(N-maleimido-methyl)cyclohexane-1-carboxylate], SMPB [Succinimidyl 4-(p-maleimido-phenyl)butyrate].

For demonstrating, the following will disclose several examples and tests of cell-penetrating drug carrier and the application thereof according to this specification. It is noted that these examples are not to limit the scope of this present invention, which should be determined in accordance with the Claims.

Example 1. Toxicity and Translocation of Cell-Penetrating Peptide and Wanted Drug In this example, we employ Indolicidin (IL; ILPWKWPWWPWRR; SEQ ID NO: 1) analogue, ILR57F89 (ILPWRWRFFPWRR; SEQ ID NO: 2) as the cell-penetrating peptide. And, doxorubicin (DOX) is chosen as the wanted drug. It should be noticed that this example is not to limit the scope of the cell-penetrating peptide and the wanted drug of this present invention.

Before looking for ideal drug carrier, it should be cared that whether the cell-penetrating peptide has serious cytotoxicity. That is because the cell-penetrating drug carrier of this specification is supposed to be applied in vivo.

In this example, HepG2 cells are individually incubated in 25 M peptide solution, 25 M DOX, and a mixed solution of 25 M DOX and 25 M peptide. And the cell viability of the mentioned HepG2 cells is followed after incubating for 1 hour and 6 hours. As shown in FIG. 1A, it can be found that all the solutions of DOX, IL (SEQ ID NO: 1), IL-R57F89 (SEQ ID NO: 2), mixture of DOX and IL, and Mixture of DOX and IL-R57F89 do not present obvious cytotoxicity to HepG2 cell.

Figure 1B:
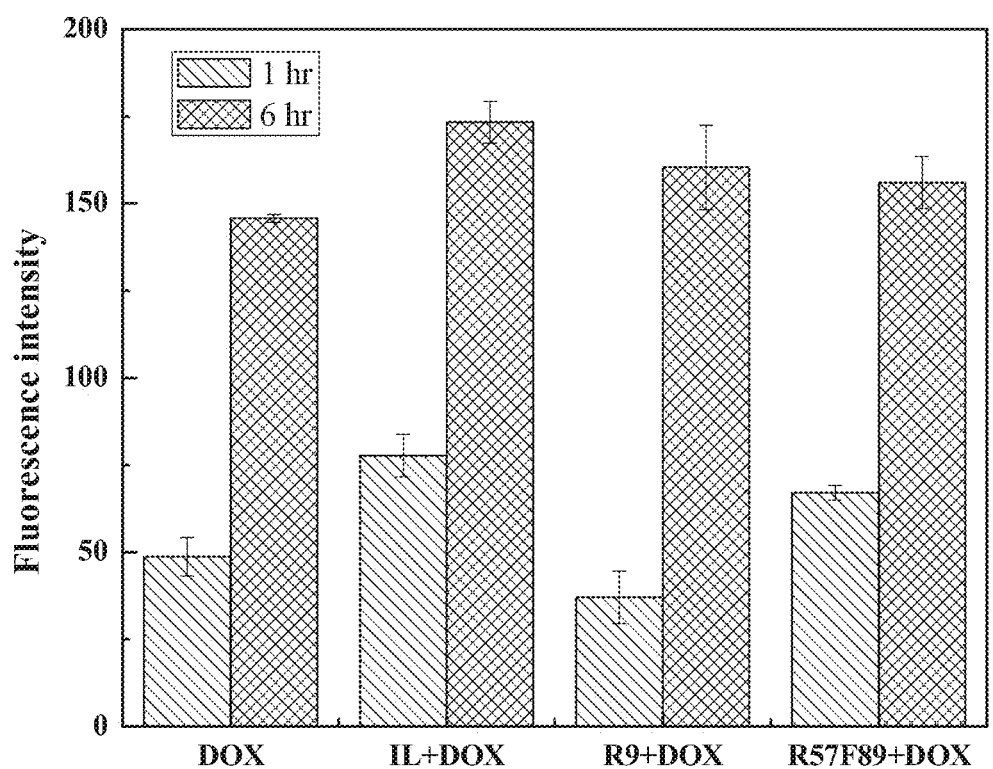
FIG. 1B shows the fluorescence intensity measured from HepG2 cytoplasm of the HepG2 individually incubated in DOX solution, mixture solution of DOX and IL, mixture solution of DOX and IL-R57F89 for 1 hour and 6 hours.

Besides, in order to ensure whether the cell-penetrating peptide is helpful to the translocation of DOX, after incubating for 1 to 6 hours, the DOX fluorescence intensity of in HepG2 tumor cell cytoplasm is measured and shown as FIG. 1B. From FIG. 1B, it can be found that for DOX solution, solution of DOX and IL mixed in equal molar ratio, and solution of DOX and IL-R57F89 mixed in equal molar ratio, the DOX fluorescence intensity of in HepG2 tumor cell cytoplasm is increased while the incubating time is from 1 hour to 6 hours. When comparing those data of incubating for 1 hour, it can be found that the fluorescence intensity of both the mixed solution of DOX and IL, and the mixed solution of DOX and IL-R57F89 are stronger than the fluorescence intensity of DOX. That is, IL (SEQ ID NO: 1) and IL-R57F89 (SEQ ID NO: 2) are really helpful to DOX translocation into cell.

Example 2. Connection Between Cell-Penetration Peptide and Wanted Drug

The wanted drug according to this specification comprises at least one primary amino group (1° amine). According to this specification, the mentioned wanted drug can connect with the cell-penetrating peptide in the following methods: (a) the primary amino group of the wanted drug connecting with the C-terminus of the cell-penetrating peptide, (b) the primary amino group of the wanted drug connecting with a first cross-linker, and the first cross-linker connecting with the C-terminus of the cell-penetrating peptide, (c) the primary amino group of the wanted drug connecting with a first cross-linker, and the first cross-linker connecting with the N-terminus of the cell-penetrating peptide.

In this example, doxorubicin (DOX), with a primary amino group, is employed as the wanted drug, and IL-R57F89 (SEQ ID NO: 2) is employed as the cell-penetrating peptide. And, sulfo-SMPB [sulfoSuccinimidyl 4-(p-maleimido-phenyl)butyrate] is employed as the first cross-linker for connecting the wanted drug and the cell-penetrating peptide.

Firstly, EDC/NHS [(1-Ethyl-3-[3-dimethylaminopropyl] carbodiimide hydrochloride)/N-Hydroxysuccinimide] is employed for activating the C-terminus of IL-R57F89 (SEQ ID NO: 2). DOX and sulfo-SMPB are reacted to form DOX-SMPB. The thiol group of the fourteenth amino acid (cysteine, abbreviated symbol as "C") of IL-R57F89 (SEQ ID NO: 2) is connected with the maleimide group of sulfo-SMPB. The primary amino group of DOX can be reacted with the sulfo-NHS group of sulfo-SMPB to form amide bonding. The connection stricture of IL-R57F89 (SEQ ID NO: 2) and DOX can be shown as the following.

Figure 2A:
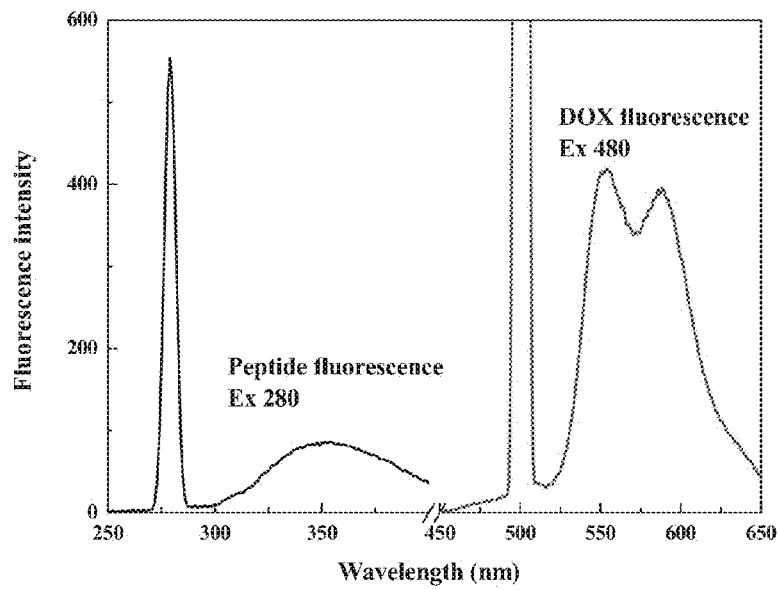
FIG. 2A shows the fluorescence intensity of IL-R57F89 and DOX.
Figure 2B:
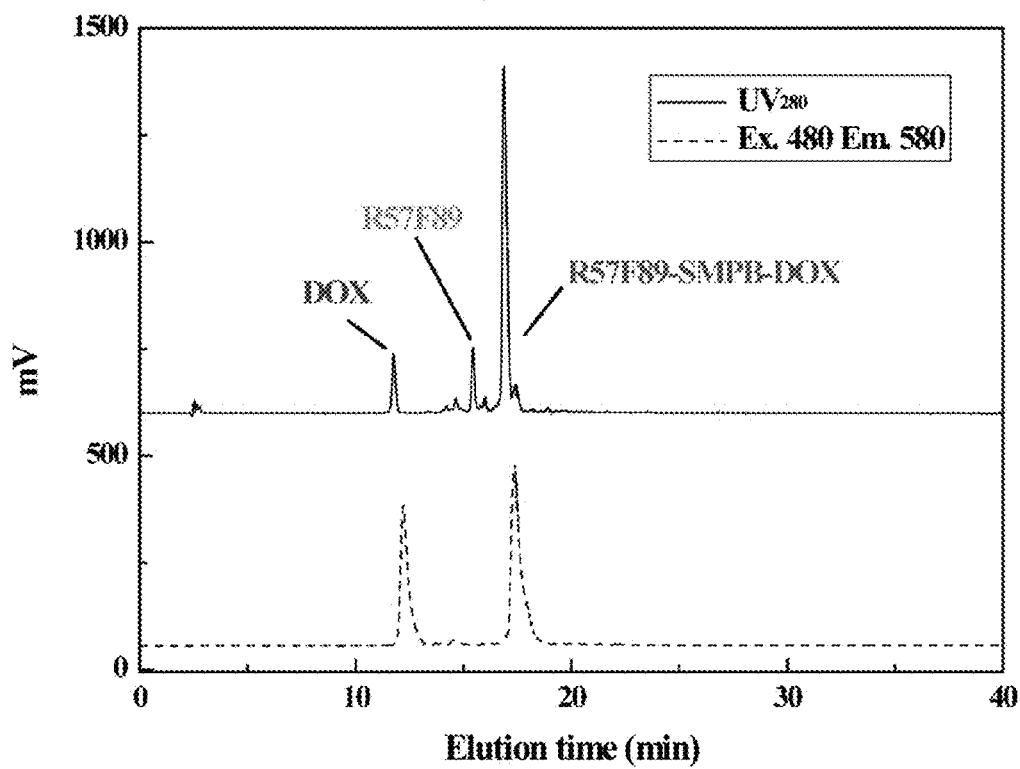
FIG. 2B shows the RP-HPLC chromatogram for monitoring the synthesis result of IL-R57F89-DOX.

RP-HPLC. From FIG. 2A, it can be found that the fluorescence emitting positions of IL-R57F89 and DOX are individually at about 280 nm and 480 nm. According to the above-mentioned fluorescence character, it can be ensured that in the reversed phase high performance liquid chromatography (RP-HPLC) analysis, the measured eluted time of IL-R57F89 and DOX is superlatively about 12 min and 16 min, and the eluted time of IL-R57F89-DOX is about 17.5 min, as shown in FIG. 2B. The gradient elution in FIG. 2B is 0.100% ACN, 50 min. The yield of the obtained IL-R57F89-DOX is about 86.4%.

Example 3. Intracellular Translocation

Figure 3:
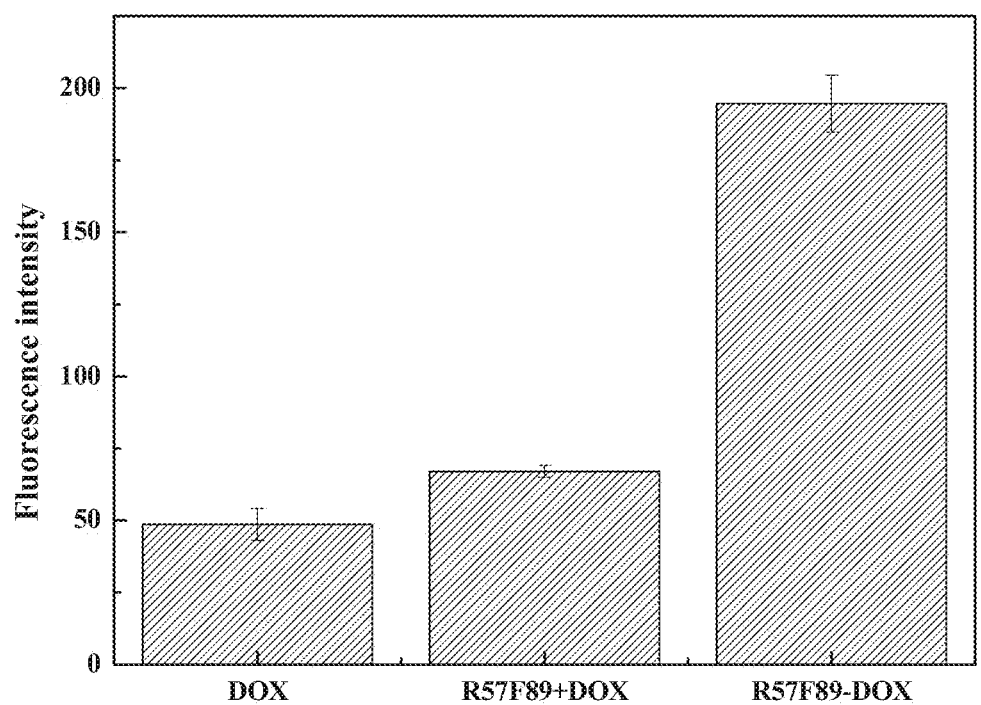
FIG. 3 shows the fluorescence intensity in cytoplasm of those HepG2 samples individually incubated in DOX, mixture of DOX and IL-R57-F89, and IL-R57-F89-DOX for 1 hour.

In this example, HepG2 cells are individually incubated in DOX, DOX and IL-R57F89 mixed solution, and IL-R57F89-DOX for 1 hour, and measured the fluorescence intensity as FIG. 3. From FIG. 3, it can be found that comparing with free DOX, there is more drug accumulation volume of DOX connected with IL-R57F89 in HepG2 cell. Estimating from the fluorescence intensity, the drug accumulation volume of IL-R57F89-DOX in HepG2 cell is about 3 times to the drug accumulation volume of DOX. Therefore, it can be found that IL-R57F89 is really helpful on carrying small molecule drug through cell membrane for increasing the drug accumulation volume of the small molecule drug in the target cell. More preferably, it also can be found that after incubating for 24 hours, the cytotoxicity of IL-R57F89-DOX is higher than the cytotoxicity of DOX.

Example 4. Selection of the Recognizable Sequence

The method of selecting the recognizable sequence is going to be presented in this example. In this example, some of the recognizable sequence is presented in this example, and these examples are not used to limit the scope of this present invention.

First of all, the selected target is cancer cell, and cancer cell can secrete matrix metalloproteinase (MMP), such as MMP-2. So that, in this example, how to find out proper

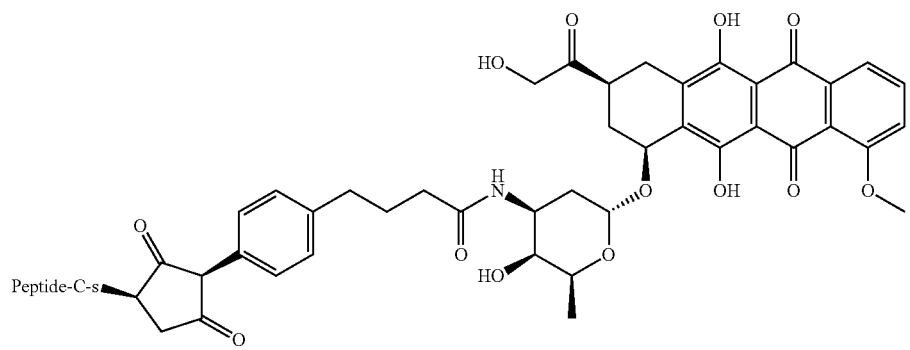

According to this example, DOX-SMPB can be formed from mixing equal volume of 500 mM DOX and 500 mM SMPB in DMSO, and the mixture of DOX and SMPB is stirred at 25° C. for 2.5 hours. 500 mM IL-R57F89 is added into the mixture and stirred at 25° C. for one night, and IL-R57F89-DOX is obtained. FIG. 2A is the fluorescence spectrum of IL-R57F89 and DOX measured with PBS buffer. The obtained IL-R57F89-DOX can be analyzed by recognizable sequence corresponding to MMP is an important point. Besides, a longer recognizable sequence needs more complex manufacture and is more expensive, especially for recognizable sequence with more than 20 amino acids. Hence, for more widely accepted and applied by industrial, in this application, we hope to find out recognizable sequence with good recognized efficiency and not with too long sequence.

Table 1 presents several recognizable sequences corresponding to MMP-2 employed in this example. In the experiment of employing MMP-2 to cut/digest recognizable sequence, after individually adding tryptophan (abbreviated symbol as "W") at the C-terminus and the N-terminus of the recognizable sequence, the digestion of the recognizable sequence by MMP-2 can be followed by the character absorption wave length at 280 nm.

TABLE 1

| Entry | MMP-2 cut-able sequence | MMP-2 recognizable sequence |
|---|---|---|
| P1 | WGPLGIAGQW | GPLG-IAGQ-ILPWRWRFFPWRR (SEQ ID NO: 7) |
| P2 | WGPLGIAGW | GPLG-IAG-ILPWRWRFFPWRR (SEQ ID NO: 8) |
| P3 | WGPLGIAIW | GPLG-IA-ILPWRWRFFPWRR (SEQ ID NO: 9) |
| P4 | WGPLGILPW | GPLG-ILPWRWRFFPWRR (SEQ ID NO: 10) |
| GPLSI-P17 | GPLSILPW . . . | GPLS-ILPWRWRFFPWRR (SEQ ID NO: 11) |

Figure 4A:
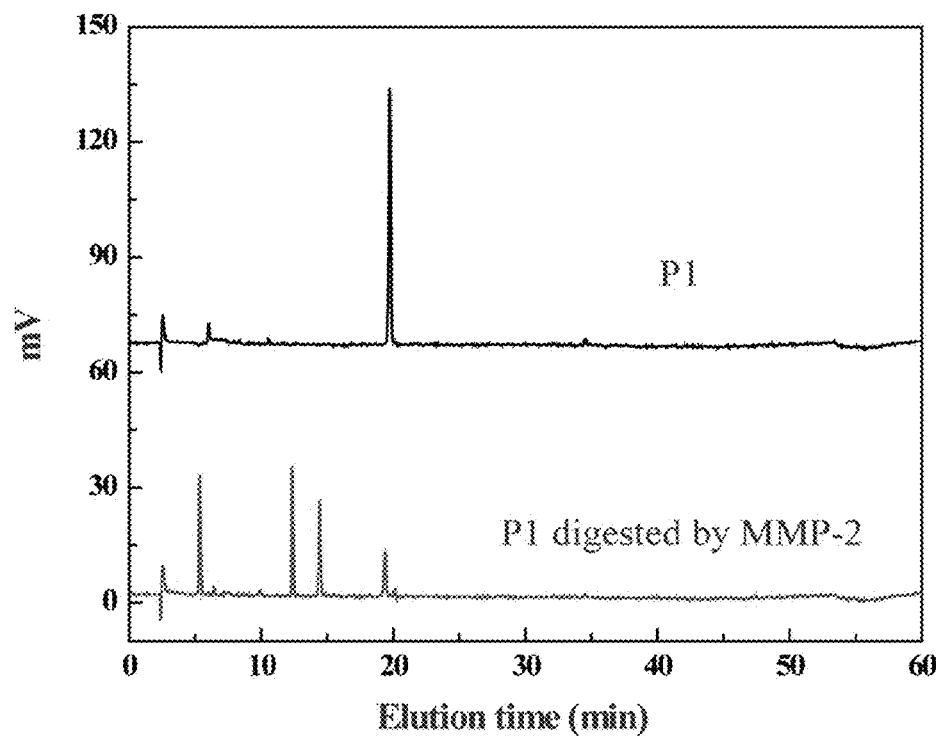
FIG. 4A to FIG. 4C respectively present the reversed-phase chromatography (RPC) chromatograms of P1, P2, and P4 digested by MMP-2.
Figure 4B:
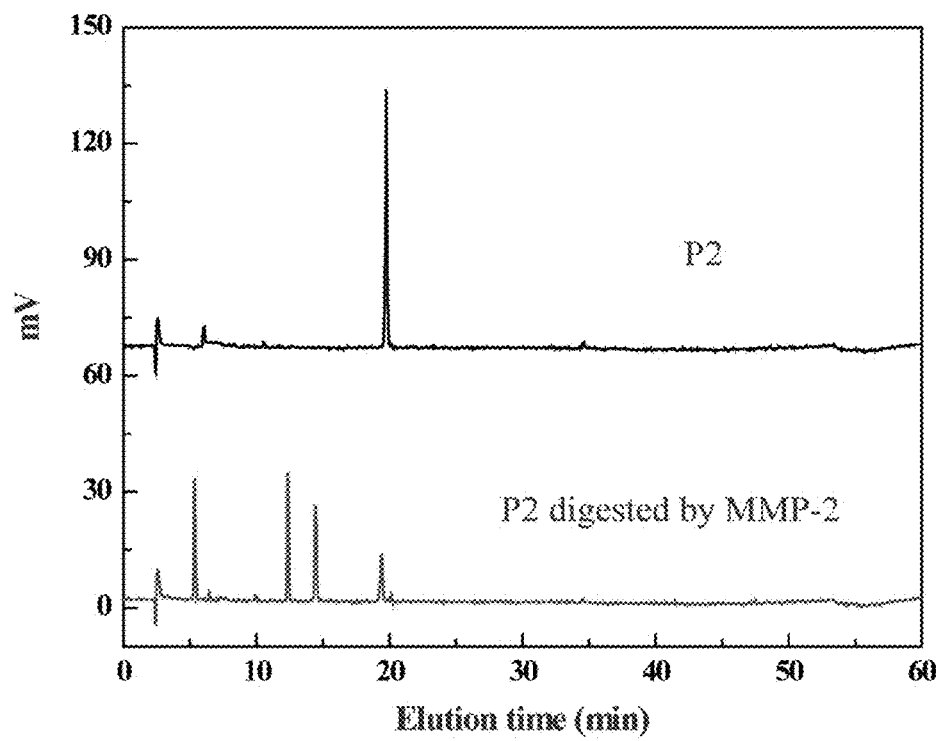
Figure 4C:
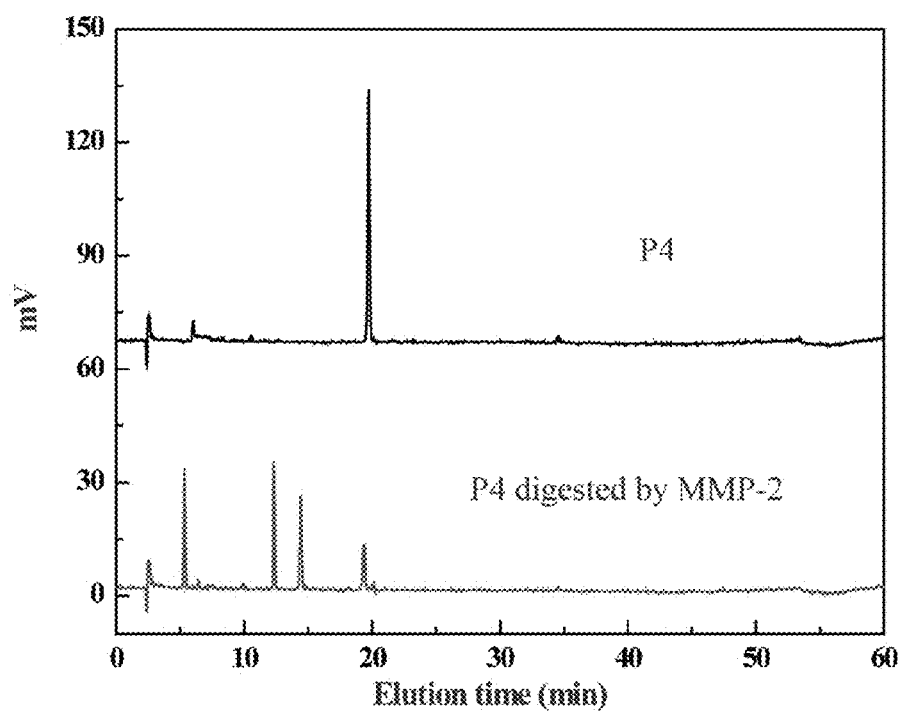

FIG. 4A to FIG. 4C respectively presents the reversed 1phase chromatography (RPC) analysis of 100 M P1, P2, and P4 in Table 1 digested by 1 g/mL MMP-2. The gradient elution is 0-100% ACN, 50 min. As shown in FIG. 4A, after digesting WGPLGIAGQW for 2 hours, the absorption peaks of the fragments of IAGQW and WGPLG are individually found at 12.5 min and 14.9 min. From this result, it can be found that the recognizable sequence with tryptophan at the N-terminus/C-terminus still can be digested by MMP-2. In P2 experiment, as shown in FIG. 4B, after digesting for 2 hours, the absorption peak of the WGPLG fragment is at 14.9 min. Besides, from FIG. 4B, it can be found that the P2 recognizable sequence is totally digested by MMP-2. In these experiments, because the P3 recognizable sequence in Table 1 cannot be dissolved in HEPES buffer, the digestion of P3 by MMP-2 cannot be measured. Another recognizable sequence P4 with the same length as P3 and different amino acid fragments is designed. And P4 is employed for the MMP-2 digestion as shown in FIG. 4C. From FIG. 4C, it can be found that after 24 hours P4 can be totally digested and the ILPW fragment is formed therefrom.

Figure 5A:
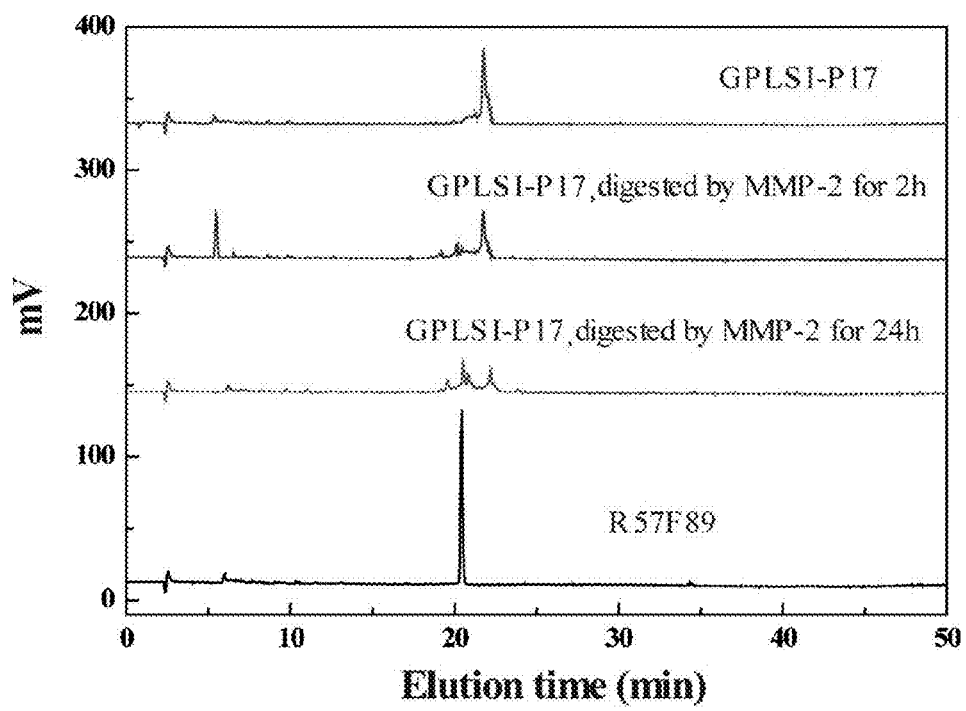
FIG. 5A and FIG. 5B respectively present the RP-HPLC chromatograms of GPLSI-P17 and GPLGI-P17 of this specification individually digested by MMP-2.
Figure 5B:
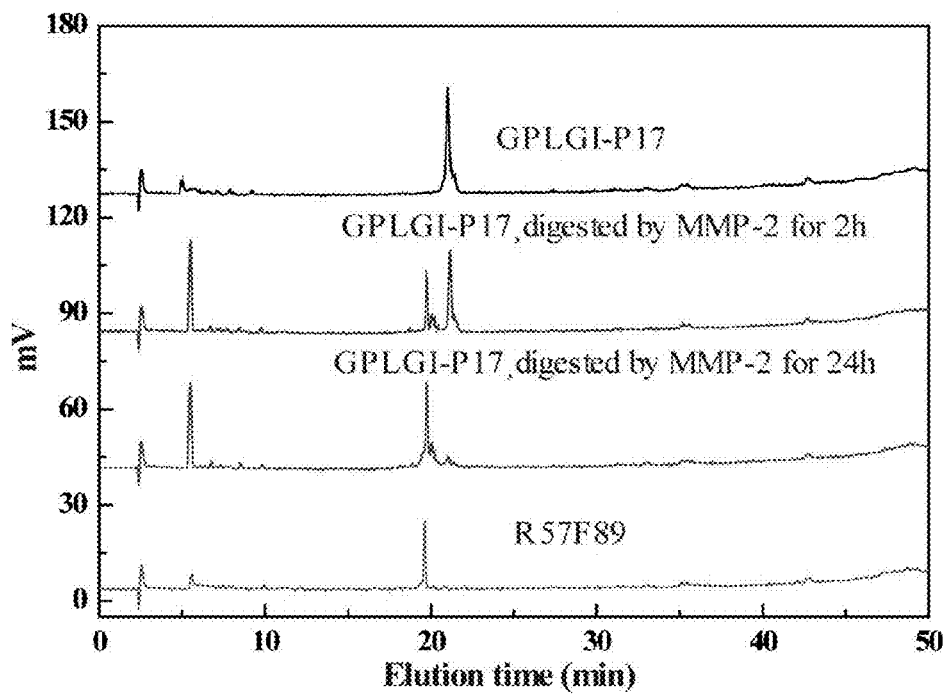

The ILPW fragment from P4 digestion and the first four amino acid fragment of IL-R57F89 are the same. There are two MMP-2 cut-able sequences, GPLSI-P17 and GPLGI-P17, designed with the sequence individually as GPLS-ILPWRWRFFPWRR (SEQ ID NO: 11) and GPLG-ILPWR-WRFFPWRR (SEQ ID NO: 10). The RP-HPLC analysis of GPLSI-P17 and GPLGI-P17 digested by MMP-2 are shown as FIG. 5A and FIG. 5B. It should be noticed that we ensure the peak of IL-R57F89 before the digestion of GPLSI-P17 and GPLGI-P17. From the retention time of IL-R57F89 in FIG. 5A and FIG. 5B, it can be found that the digestion of MMP-2 will be happened at the bonding between serine (Ser) and glycine (Gly) at the C-terminus of IL-R57F89. Moreover, from FIG. 5A and FIG. 5B, it also can be found that GPLSI-P17 and GPLGI-P17 individually can be totally digested by MMP-2 after 24 hours. Therefore, GPLSI-P17 and GPLGI-P17 can be employed as the recognizable sequence of this application.

Example 5. Protease Stability Test

It can be expected that drug carrier in vivo circulation will face to many bio-enzymes, wherein those bio-enzymes will cut the drug carrier. Before designing proper protection to those bio-enzymes, we hope to finger out the cutting result of the recognizable sequence-CPP (cell-penetrating peptide) by bio-enzymes. In this example, trypsin is employed as the bio-enzyme. Trypsin is a protease with selectivity, especially for cutting the carboxyl side of arginine (R) or lysine (K) of protein or peptide. In this example, when CPP is IL-R57F89, there are four arginine fragments in CPP being able to be cut by trypsin. Those four arginine fragments are R5, R7, R12, and R13. When IL-R57F89 totally digested by trypsin, three fragments as 11-R5, W6-R7, and F8-R12 will be obtained. In this example, the digestion of GPLSI-P17 by trypsin is followed by RPC with UV280, and it can be found that three fragments as G1-R9, W10-R11, and F12-R16 can be obtained after totally digested.

Figure 6A:
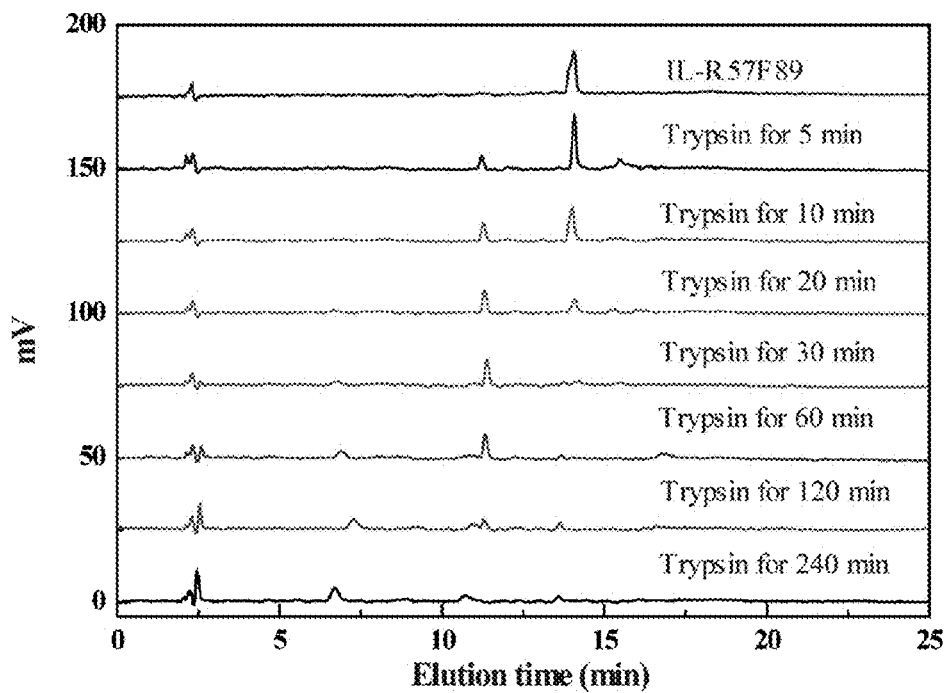
FIG. 6A and FIG. 6B respectively present the RPC-UV280 chromatograms of IL-R57F89 and GPLSI-P17 digested by trypsin.
Figure 6B:
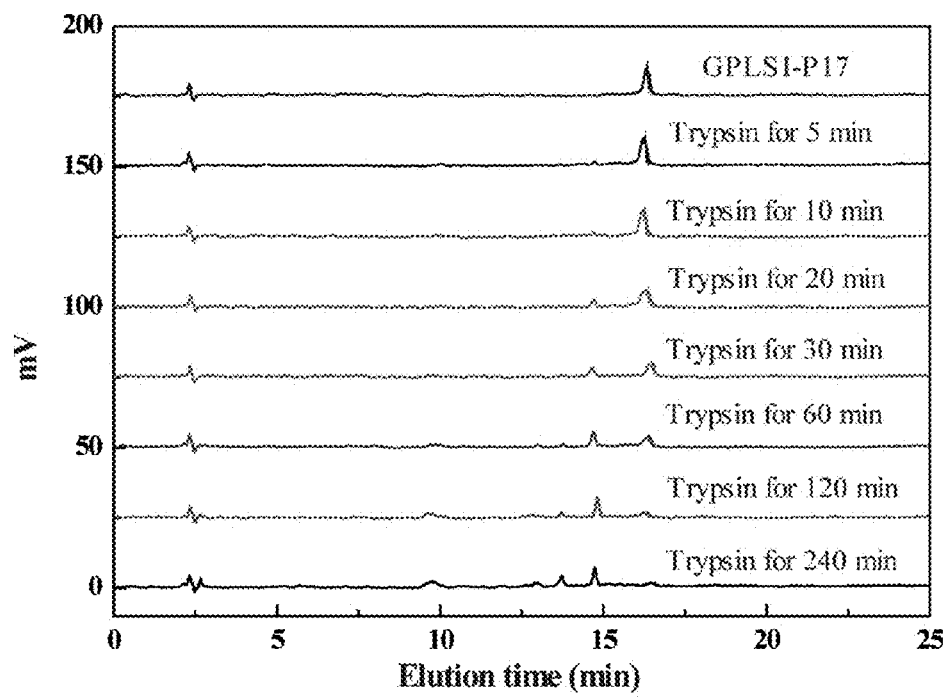
Figure 6C:
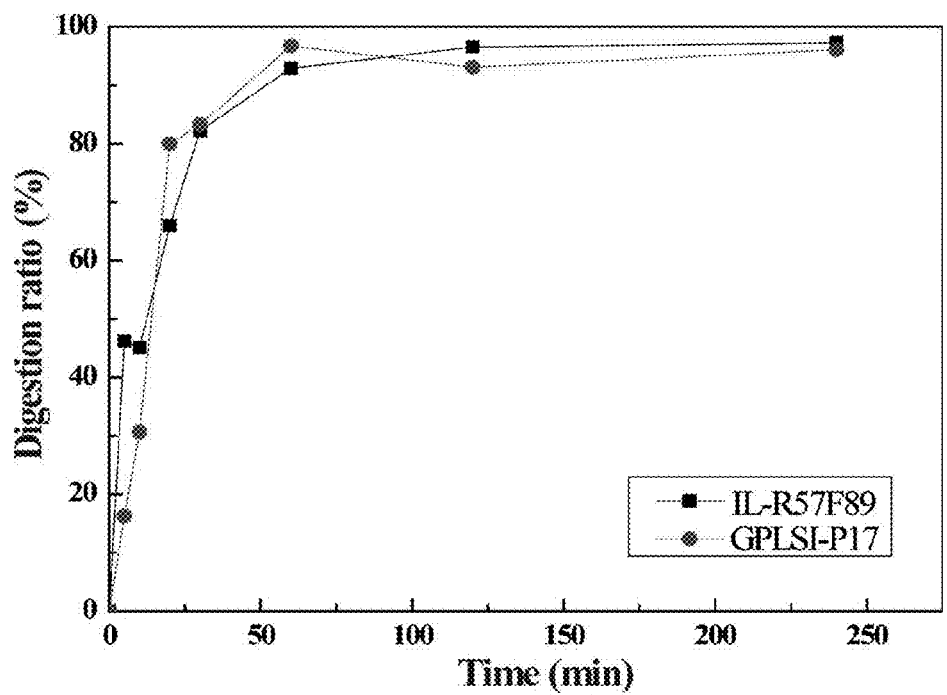
FIG. 6C presents the digested ratio diagram of IL-R57F89 and GPLSI-P17 calculated from the results in FIG. 6A and FIG. 6B.

FIG. 6A and FIG. 6B are respectively the RPC-UV280 spectra of IL-R57F89 and GPLSI-P17 digested by 0.1 g/mL trypsin. The gradient elution is 20-70% ACN, 5-30 min. In the spectra, there are sampling analysis results of 5, 10, 20, 30, 60, 120, and 240 min from top to bottom. From FIG. 6A and FIG. 6B, it can be found that IL-R57F89 and GPLSI-P17 are almost digested completely by trypsin after 2 hours. FIG. 6C shows the digestion ratio diagram of IL-R57F89 and GPLSI-P17 from FIG. 6A and FIG. 6B. From FIG. 6C, it can be found that about 90-95% IL-R57F89 and GPLSI-P17 are digested by trypsin after about 1 hour. According to this example, it can be noticed that it has to design a proper structure for keeping the recognizable sequence-CPP of drug carrier from cut by bio-enzyme(s) before the drug carrier achieving the target cell.

Example 6. Selection of the Bioinert Polymer

In this example, it illustrates how to select a proper bioinert polymer. It should be noticed that this example just presents the best model of the bioinert polymer. One skilled in this art can select similar bioinert polymer according to this application. So that the bioinert polymer of this invention is not limited by this example.

From the above example, it is possible that the recognizable sequence-CPP, such as GPLSI-P17, of drug carrier of this application cut by other bio-enzyme(s) during circulation before the drug carrier achieving the target cell. In order to decreasing the disturbance from other bio-enzyme(s), it is necessary to introduce a bioinert polymer to protect the recognizable sequence-CPP. According to this application, the bioinert polymer can keep the recognizable sequence-CPP from cut by other bio-enzyme(s), and can expose part of the recognizable sequence for anchoring by the target cell.

Figure 7A:
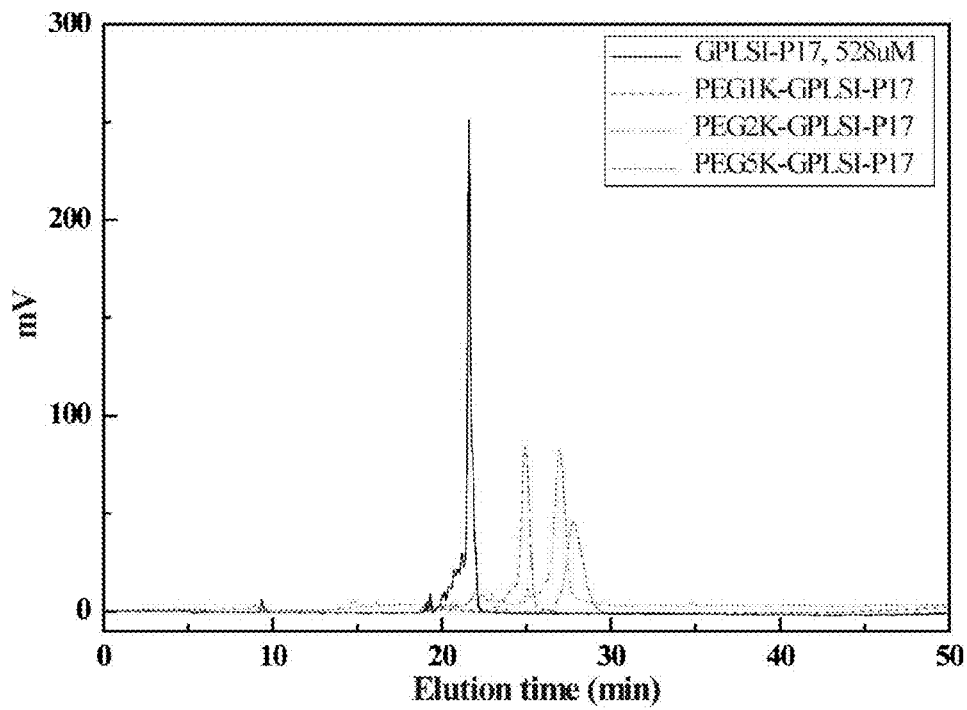
FIG. 7A shows the RPC chromatograms of the results of GPLSI-P17, PEG (average molecular weight about 1 KDa) reacting with GPLSI-P17, PEG (average molecular weight about 2 KDa) reacting with GPLSI-P17, and PEG (average molecular weight about 5 KDa) reacting with GPLSI-P17.

In this example, PEG is employed as the bioinert polymer. Firstly, PEGs with different molecular weight are linked to GPLSI-P17. SPA modified PEG is linked to the N-terminus of the recognizable sequence-CPP. The reacting condition is at 37° C. in pH 7.4 PBS buffer for 24 hours. In the above reaction, the molar ratio of PEG and the recognizable sequence-CPP is about 4. FIG. 7A shows the RPC spectra of 528 M GPLSI-P17, PEG (average molecular weight 1 KDa) added to GPLSI-P17, PEG (average molecular weight 2 KDa) added to GPLSI-P17, and PEG (average molecular weight 5 KDa) added to GPLSI-P17. The gradient elution is 0-100% ACN, 50 min. From FIG. 7a, it can be found that the retention time of GPLSI-P17 is about 21.8 min, and all the recognizable sequence-CPPs are linked with PEG in the above reactions.

Figure 7B:
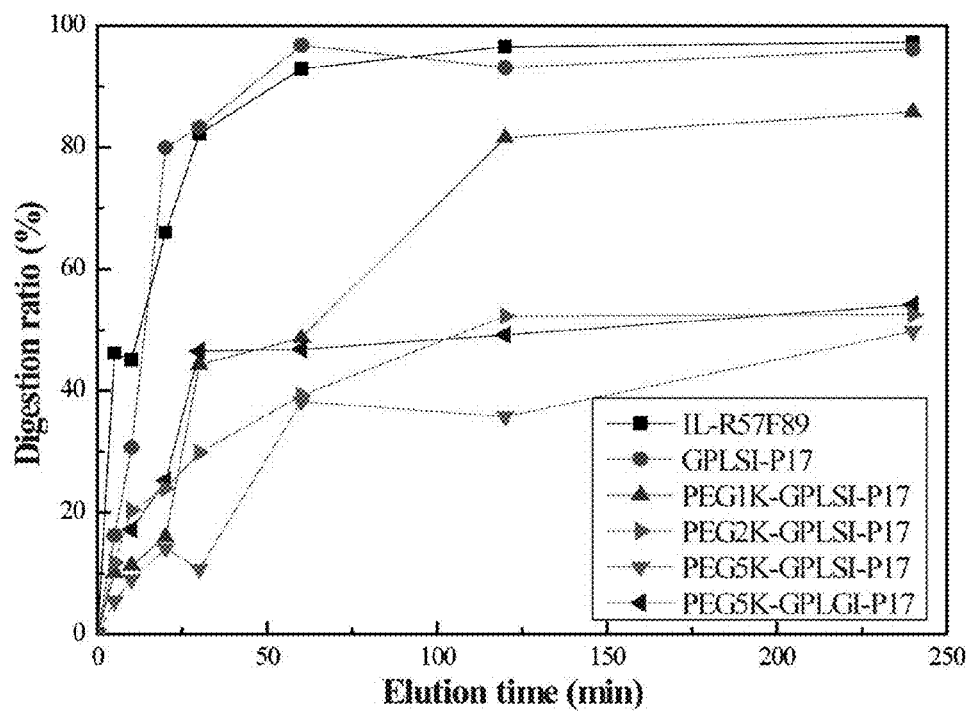
FIG. 7B shows the digestion ratio diagrams of IL-R57F89, GPLSI-P17, PEG1K-GPLSI-P17, PEG2K-GPLSI-P17, PEG5K-GPLSI-P17, and PEG5K-GPLGI-P17 digested by trypsin.

Subsequently, it is important to find out proper PEG length so that the PEG can provide protection to the recognizable sequence-CPP and the PEG will not impact the anchoring of the target cell to the recognizable sequence. FIG. 7B presents the trypsin digestion results of IL-R57F89, GPLSI-P17, PEG1K-GPLSI-P17, PEG2K-GPLSI-P17, PEG5K-GPLSI-P17, and PEG5K-GPLGI-P17. Referred to FIG. 7B, it can be found that IL-R57F89 and GPLSI-P17 are almost digested completely after about 1 hour. PEG1K-GPLSI-P17 is digested about 80% after 2 hours. After digesting for 4 hours, PEG2K-GPLSI-P17 and PEGSK-GPLSI-P17 are individually digested about 50% and 45%. It can be ensured that the PEG with proper length can efficiently keep the recognizable sequence-CPP from digested by bio-enzyme. And, when adjusting the PEG length with the length of the recognizable sequence-CPP, the protection of the PEG to the recognizable sequence-CPP can be optimized. For example, to those general recognizable sequence-CPP now, the proper length of PEG is about 1000-25000 Da.

Figure 8A:
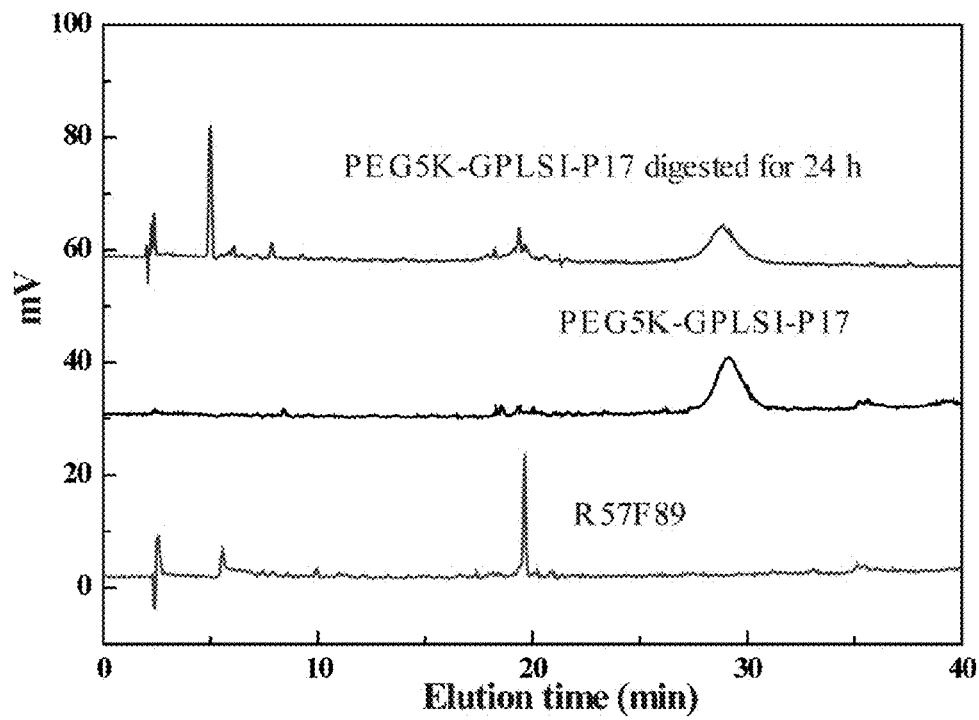
FIG. 8A shows the RPC chromatograms of PEG5K-GPLSI-P17, PEG2K-GPLSI-P17, IL-R57F89, from top to bottom, individually digested by MMP-2 for 24 hours.
Figure 8B:
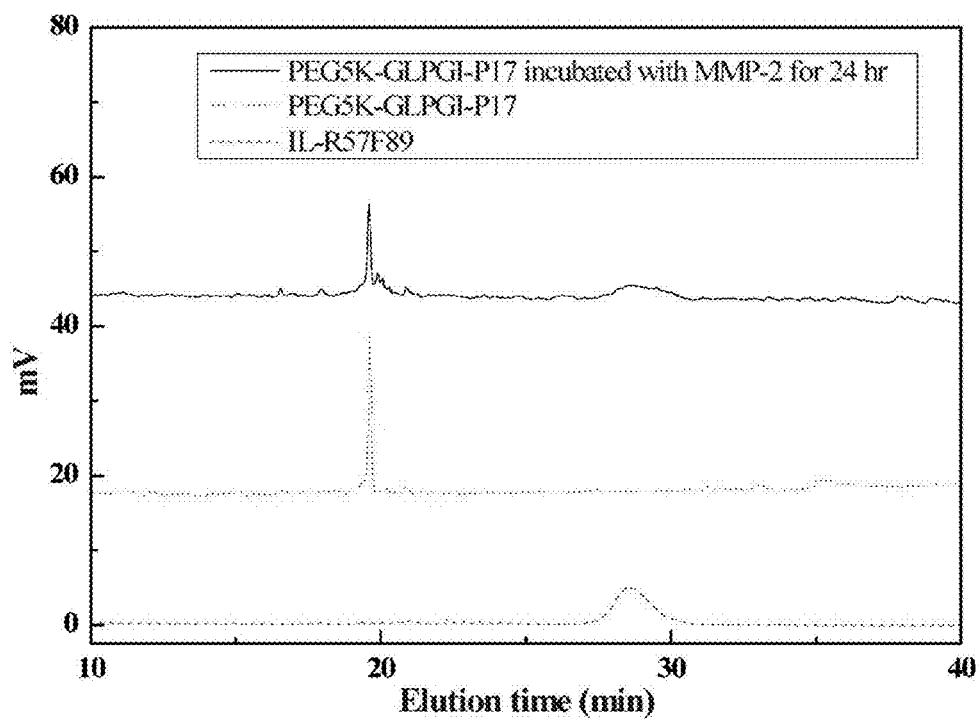
FIG. 8B shows the RPC chromatograms of PEG2K-GPLGI-P17, PEG5K-GPLGI-P17, IL-R57F89, from top to bottom, individually digested by MMP-2 for 24 hours.

Including providing protection to recognizable sequence-CPP, proper PEG length will not impact the anchoring of the target cell to the recognizable sequence. Therefore, we try to finger out the effect of the PEG length to the following anchoring. PEG5K-GPLSI-P17 and PEG5K-GPLGI-P17 are individually dissolved in pH 7.4 HEPES buffer. MMP-2 is added into the above solutions and the final concentration is about 1 g/mL. The solutions are independently reacted at 37° C. for 24 hours. The reaction results are analyzed by RPC and shown as FIG. 8A and FIG. 8B. Referred to FIG. 8A and FIG. 8B, it can be found that both PEGSK-GPLSI-P17 and PEGSK-GPLGI-P17 can be digested by MMP-2. It also can be found that the digestion ratio of PEGSK-GPLSI-P17 is higher than the digestion ratio of PEGSK-GPLGI-P17. After digested by MMP-2 for 4 hours, the digestion ratio of PEGSK-GPLGI-P17 is about 38.8%, lower than the digestion ratio of PEGSK-GPLSI-P17, about 52%, under the same digesting condition.

Example 7. Small Molecule Drug and Drug Carrier

Figure 9:
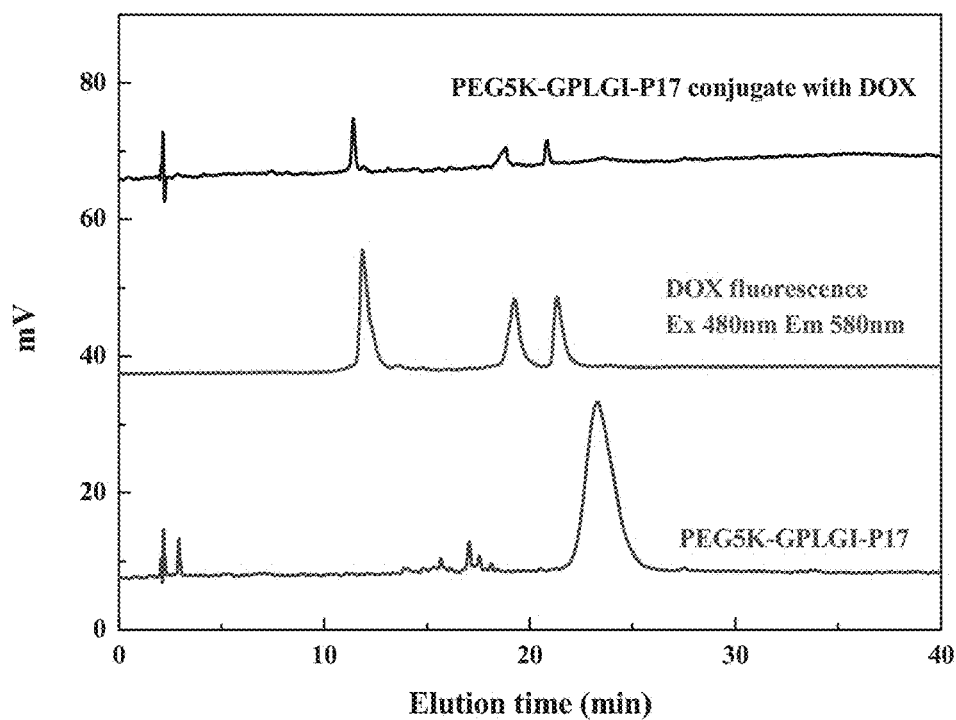
FIG. 9 shows the RPC chromatogram of the synthesis result of PEG5K-GPLGI-P17-DOX of this specification.

In this example, PEGSK-GPLGI-P17-DOX is synthesized. After reacting with EDC/NHS for 1 hour, the carboxyl group at the C-terminus of DOX is activated. In order to connect DOX to the C-terminus of PEGSK-GPLGI-P17, the DOX solution is added into the PBS buffer with PEGSK-GPLGI-P17. After reacting for 4 hours, the reacting result is analyzed by RPC and shown as FIG. 9. From FIG. 9, it can be found that PEG5K-GPLGI-P17 is actually connected to DOX, and the retention time of the product is about 19 min.

Figure 10:
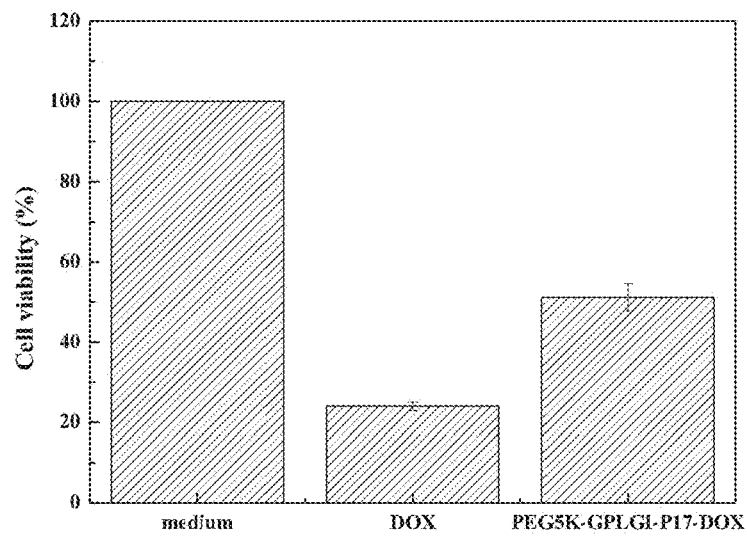
FIG. 10 shows the cell viability diagrams of HepG2 cells individually reacted with DOX and PEG5K-GPLGI-P17-DOX for 24 hours.

DOX and PEG5K-GPLGI-P17-DOX are processed cytotoxicity test. When DOX and PEG5K-GPLGI-P17-DOX are separately acted on HepG2 cell for 24 hour, the measured cell viability is shown as FIG. 10. From FIG. 10, it can be found that both DOX and PEG5K-GPLGI-P17-DOX can efficiently decrease the cell viability of HepG2. It also can be found from FIG. 10 that the cytotoxicity of PEG5K-GPLGI-P17-DOX is lower than the cytotoxicity of DOX. That is possibly because the recognizable sequence of PEG5K-GPLGI-P17-DOX is not completely digested by MMP-2 in the reacting time, and PEG does not totally break away from GPLGI-P17-DOX. So that the dosage entering the target cell is decreased.

In summary, this invention discloses cell-penetrating drug carrier and the application thereof. The cell-penetrating drug carrier comprises cell-penetrating peptide, recognizable sequence, and bioinert polymer. According to this specification, in order to specifically delivery wanted drug to target cell, the recognizable sequence of the mentioned cell-penetrating drug carrier can be selected/modified with the target cell. Through carrying the wanted drug into the cytoplasm of the target cell, the drug accumulation volume in the target cell can be efficiently increased. According to the employed cell-penetrating peptide and the recognizable sequence, a bioinert polymer with proper length is selected for decreasing the digestion of the cell-penetrating peptide and the recognizable sequence before approaching the target cell. And, the bioinert polymer will not impact the recognizable sequence cut to release the cell-penetrating peptide and the wanted drug while the cell-penetrating drug carrier is nearby the target cell. Preferably, according to this specification, the mentioned cell-penetrating drug carrier can further comprise a cross-linker. The mentioned cross-linker is located at least one of the following position: between cell-penetrating peptide and wanted drug, between cell-penetrating peptide and recognizable sequence, and between recognizable sequence and bioinert polymer. The mentioned cross-linker can be peptide with 3-5 amino acids. The cross-linker can be employed for increasing the connection of those items at both sides of the cross-linker, or the cross-linker can be employed for adjusting the total length of the cell-penetrating drug carrier. According to this specification, the cell-penetrating drug carrier can efficiently carrying small molecule drug into cytoplasm of the target cell. More preferably, through selecting proper bioinert polymer, the decomposed time of the cell-penetrating drug carrier in vivo circulation can be slow-down to about 24 times. According to this specification, the cell-penetrating drug carrier can provide excellent specific delivery, and can efficiently increase the drug accumulation volume in target cell. More preferably, comparing to those existing drug carrier, this specification discloses a cell-penetrating drug carrier with adjustable length and with non-expensive manufacturing cost.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A cell-penetrating drug carrier, comprising:
   a cell-penetrating peptide (CPP), said cell-penetrating peptide connected with a wanted drug, wherein said wanted drug comprises at least one primary amino group (1° amine), wherein said cell-penetrating peptide is ILR57F89 (ILPWRWRFFPWRR; SEQ ID NO: 2);
   a recognizable sequence connected with said cell-penetrating peptide, wherein said recognizable sequence is selected from the group consisting of Gly-Pro-Leu-Ser-Ile (SEQ ID NO: 3) and Gly-Pro-Leu-Gly-Ile (SEQ ID NO: 4); and
   a bioinert polymer directly connected with said recognizable sequence.

2. The cell-penetrating drug carrier according to claim 1, wherein said recognizable sequence is a peptide wherein said peptide can be recognized by matrix metalloproteinase (MMP).

3. The cell-penetrating drug carrier according to claim 1, wherein said bioinert polymer is polyethylene glycol (PEG).

4. The cell-penetrating drug carrier according to claim 1, wherein the average molecular weight of said bioinert polymer is 1000-25000 Da.

5. The cell-penetrating drug carrier according to claim 1, further comprises a first cross-linker between said cell-penetrating peptide and said wanted drug, wherein said first cross-linker comprises peptide consisted of 3 to 5 amino acids.

6. The cell-penetrating drug carrier according to claim 1, further comprises a second cross-linker between said cell-penetrating peptide and said recognizable sequence, wherein said second cross-linker comprises peptide consisted of 3 to 5 amino acids.

7. The cell-penetrating drug carrier according to claim 1, further comprises a third cross-linker between said recognizable sequence and said bioinert polymer, wherein said third cross-linker comprises peptide consisted of 3 to 5 amino acids.

8. A cell-penetrating drug carrier, comprising:
   a cell-penetrating peptide (CPP), said cell-penetrating peptide connected with a wanted drug, wherein said cell-penetrating peptide is ILR57F89 (ILPWRWRFFPWRR; SEQ ID NO: 2), wherein said wanted drug comprises at least one primary amino group (1° amine);
   a recognizable sequence connected with said cell-penetrating peptide, wherein said recognizable sequence is peptide being able to be recognized by matrix metalloproteinase (MMP), wherein said recognizable sequence is selected from the group consisting of Gly-Pro-Leu-Ser-Ile (SEQ ID NO: 3) and Gly-Pro-Leu-Gly-Ile (SEQ ID NO: 4); and
   a bioinert polymer connected with said recognizable sequence.

9. The cell-penetrating drug carrier according to claim 8, wherein said matrix metalloproteinase (MMP) is selected from the group consisting of MMP-2 and MMP-9.

10. The cell-penetrating drug carrier according to claim 8, wherein said recognizable sequence is selected from one of the group consisting of the following: Gly-Pro-Leu-Ser-Ile (SEQ ID NO: 3), Gly-Pro-Leu-Gly-Ile (SEQ ID NO: 4), wherein the "Ile" in said recognizable sequence is from said cell-penetrating peptide.

11. The cell-penetrating drug carrier according to claim 8, wherein said bioinert polymer is polyethylene glycol (PEG).

12. The cell-penetrating drug carrier according to claim 8, wherein the average molecular weight of said bioinert polymer is 1000-25000 Da.

13. The cell-penetrating drug carrier according to claim 8, further comprises a first cross-linker between said cell-penetrating peptide and said wanted drug, wherein said first cross-linker comprises peptide consisted of 3 to 5 amino acids.

14. The cell-penetrating drug carrier according to claim 8, further comprises a second cross-linker between said cell-penetrating peptide and said recognizable sequence, wherein said second cross-linker comprises peptide consisted of 3 to 5 amino acids.

15. The cell-penetrating drug carrier according to claim 8, further comprises a third cross-linker between said recognizable sequence and said bioinert polymer, wherein said third cross-linker comprises peptide consisted of 3 to 5 amino acids.

* * * * *

SEQUENCE LISTING

<160> NUMBER OF SEQ ID NOS: 11

<210> SEQ ID NO 1
<211> LENGTH: 13
<212> TYPE: PRT
<213> ORGANISM: Artificial Sequence
<220> FEATURE:
<223> OTHER INFORMATION: bovine

<400> SEQUENCE: 1

Ile Leu Pro Trp Lys Trp Pro Trp Trp Pro Trp Arg Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: the sequence is synthesized

<400> SEQUENCE: 2

Ile Leu Pro Trp Arg Trp Arg Phe Phe Pro Trp Arg Arg
1               5                   10

<210> SEQ ID NO 3
<211> LENGTH: 5
<212> TYPE: PRT
<213> ORGANISM: Artificial Sequence
<220> FEATURE:
<223> OTHER INFORMATION: the sequence is synthesized

<400> SEQUENCE: 3

Gly Pro Leu Ser Ile
1               5

<210> SEQ ID NO 4
<211> LENGTH: 5
<212> TYPE: PRT
<213> ORGANISM: Artificial Sequence
<220> FEATURE:
<223> OTHER INFORMATION: the sequence is synthesized

<400> SEQUENCE: 4

Gly Pro Leu Gly Ile
1               5

<210> SEQ ID NO 5
<211> LENGTH: 4
<212> TYPE: PRT
<213> ORGANISM: Artificial Sequence
<220> FEATURE:
<223> OTHER INFORMATION: the sequence is synthesized

<400> SEQUENCE: 5

Gly Pro Leu Ser
1

<210> SEQ ID NO 6
<211> LENGTH: 4
<212> TYPE: PRT
<213> ORGANISM: Artificial Sequence
<220> FEATURE:
<223> OTHER INFORMATION: the sequence is synthesized

<400> SEQUENCE: 6

Gly Pro Leu Gly
1

<210> SEQ ID NO 7
<211> LENGTH: 21
<212> TYPE: PRT
<213> ORGANISM: Artificial Sequence
<220> FEATURE:
<223> OTHER INFORMATION: the sequence is synthesized

<400> SEQUENCE: 7

Gly Pro Leu Gly Ile Ala Gly Gln Ile Leu Pro Trp Arg Trp Arg Phe
1               5                   10                  15

Phe Pro Trp Arg Arg
            20

<210> SEQ ID NO 8
<211> LENGTH: 20
<212> TYPE: PRT
<213> ORGANISM: Artificial Sequence
<220> FEATURE:
<223> OTHER INFORMATION: the sequence is synthesized

<400> SEQUENCE: 8

Gly Pro Leu Gly Ile Ala Gly Ile Leu Pro Trp Arg Trp Arg Phe Phe
1               5                   10                  15

Pro Trp Arg Arg
        20

<210> SEQ ID NO 9
<211> LENGTH: 19
<212> TYPE: PRT
<213> ORGANISM: Artificial Sequence
<220> FEATURE:
<223> OTHER INFORMATION: the sequence is synthesized

<400> SEQUENCE: 9

Gly Pro Leu Gly Ile Ala Ile Leu Pro Trp Arg Trp Arg Phe Phe Pro
1               5                   10                  15

Trp Arg Arg

<210> SEQ ID NO 10
<211> LENGTH: 17
<212> TYPE: PRT
<213> ORGANISM: Artificial Sequence
<220> FEATURE:
<223> OTHER INFORMATION: the sequence is synthesized

<400> SEQUENCE: 10

Gly Pro Leu Gly Ile Leu Pro Trp Arg Trp Arg Phe Phe Pro Trp Arg
1               5                   10                  15

Arg

<210> SEQ ID NO 11
<211> LENGTH: 17
<212> TYPE: PRT
<213> ORGANISM: Artificial Sequence
<220> FEATURE:
<223> OTHER INFORMATION: the sequence is synthesized

<400> SEQUENCE: 11

Gly Pro Leu Ser Ile Leu Pro Trp Arg Trp Arg Phe Phe Pro Trp Arg
1               5                   10                  15

Arg